(12) United States Patent
Healey et al.

(10) Patent No.: US 8,245,384 B2
(45) Date of Patent: Aug. 21, 2012

(54) MODULAR CONVERTING LINE FOR FABRICATING ABSORBENT ARTICLES

(75) Inventors: Patrick John Healey, West Chester, OH (US); Stoyan Lokar, Mason, OH (US); Daniel Jon Amundson, Cincinnati, OH (US); James Jay Benner, Morrow, OH (US); Jose Mauricio Berrizbeitia, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 478 days.

(21) Appl. No.: 12/544,302

(22) Filed: Aug. 20, 2009

(65) Prior Publication Data

US 2011/0041325 A1    Feb. 24, 2011

(51) Int. Cl.
*B23P 19/00* (2006.01)
*B65G 65/00* (2006.01)
(52) U.S. Cl. .......................... 29/650; 29/426.1; 414/800
(58) Field of Classification Search .................... 29/650, 29/779, 401.1, 426.1, 428, 426.4, 464, 469, 29/419.1, 2.23; 414/800; 52/79.1, 745.19; 156/269, 459, 536
See application file for complete search history.

(56) References Cited

U.S. PATENT DOCUMENTS

| | | |
|---|---|---|
| 3,860,003 A | 1/1975 | Buell |
| 4,472,783 A | 9/1984 | Johnstone et al. |
| 5,151,092 A | 9/1992 | Buell et al. |
| 5,383,988 A | 1/1995 | Herrmann et al. |
| 5,492,591 A | 2/1996 | Herrmann et al. |
| 5,554,145 A | 9/1996 | Roe et al. |
| 5,569,234 A | 10/1996 | Buell et al. |
| 5,580,411 A | 12/1996 | Nease et al. |
| 5,868,899 A | 2/1999 | Gundersen |
| 6,004,306 A | 12/1999 | Robles et al. |
| 6,074,333 A | 6/2000 | Rajala et al. |
| 6,349,237 B1 | 2/2002 | Koren et al. |
| 6,574,520 B1 | 6/2003 | Liu et al. |
| 6,788,987 B2 | 9/2004 | Slechta et al. |
| 6,990,715 B2 | 1/2006 | Liu et al. |

(Continued)

FOREIGN PATENT DOCUMENTS

DE    40 18 266 A1    12/1991

(Continued)

OTHER PUBLICATIONS

PCT International Search Report, dated Feb. 1, 2011, 12 pages.

*Primary Examiner* — John C Hong
(74) *Attorney, Agent, or Firm* — Charles R. Matson

(57) ABSTRACT

The present disclosure relates to converting lines for manufacturing absorbent articles. The converting lines include a plurality of process equipment converting modules connected with each other along a machine direction (MD). Adjacent converting modules may be releasably connectable to each other with converting module couplers. The converting modules may also have substantially identical dimensions, wherein each converting module defines the same or substantially the same MD length, CD width, and height. The converting modules may also be sized to be received within a standard shipping container. The converting lines may includes a plurality of accessory service modules supported by respective converting modules and connected with each other along the machine directions. The accessory service modules may also be adapted to be received within standard shipping containers. Adjacent accessory service modules may be releasably connected to each other with accessory module couplers, which may include quick-disconnect couplers.

20 Claims, 16 Drawing Sheets

U.S. PATENT DOCUMENTS

| | | |
|---|---|---|
| 2002/0148548 A1 | 10/2002 | Murie et al. |
| 2002/0151422 A1 | 10/2002 | Duhm et al. |
| 2004/0162536 A1 | 8/2004 | Becker et al. |
| 2006/0286343 A1 | 12/2006 | Curro et al. |
| 2007/0197987 A1 | 8/2007 | Tsang et al. |
| 2007/0213678 A1 | 9/2007 | Thorson et al. |
| 2010/0078119 A1 | 4/2010 | Yamamoto |
| 2010/0170202 A1 | 7/2010 | Bray et al. |
| 2011/0041417 A1* | 2/2011 | Healey et al. .................. 52/79.1 |
| 2011/0041997 A1* | 2/2011 | Benner et al. ................ 156/269 |

FOREIGN PATENT DOCUMENTS

| | | |
|---|---|---|
| DE | 10 2006 017379 A1 | 10/2007 |
| EP | 0 589 859 A1 | 3/1994 |
| EP | 1 174 377 A2 | 1/2002 |
| EP | 1188426 B1 | 10/2008 |
| WO | WO 00/38608 A1 | 7/2000 |
| WO | WO 01/56523 A1 | 8/2001 |
| WO | WO 01/56524 A1 | 8/2001 |
| WO | WO 2005/005296 A1 | 1/2005 |

* cited by examiner

MODULAR CONVERTING LINE FOR FABRICATING ABSORBENT ARTICLES

FIELD OF THE INVENTION

The present disclosure relates to converting lines for manufacturing absorbent articles, and more particularly, to converting lines having process equipment modules and modular accessory service ducts adapted for flexible installation, removal, replacement, and shipping.

BACKGROUND OF THE INVENTION

Disposable, reusable and durable products such as diapers, adult incontinence articles, feminine hygiene tampons, sanitary napkins, underpants, shirts, shorts, swimsuits, gowns, pants, coats, gloves, scarves, surgical drapes, bibs, blankets, sheets, pillow cases, etc. may be manufactured on high speed converting lines. A converting line may utilize a web-based carrier to which many source materials, whether in a continuous web or discrete pieces, are processed and/or attached to the web to create a finished product.

Although a converting line may allow for high speed production, some converting lines may be inflexible in that line changes are time consuming and expensive. For example, some converting lines may require extensive disassembly and reassembly when conducting maintenance and/or replacing certain components. In another example, converting lines may require substantial disassembly and rework in order to accommodate product upgrades. In one scenario, a product upgrade may, for example, require the following steps: constructing manual or handmade products incorporating the upgrade in order to test the concept and determine consumer acceptance of such an upgrade; constructing a machine production unit that may manufacture the product upgrade and/or the entire product incorporating the upgrade in order to determine product and process feasibility; constructing a high speed test stand that may manufacture the product upgrade in isolation at high speeds in order to test the feasibility of high speed manufacturing; constructing a prototype line that is able to make complete prototype products at high speeds; reconstructing a high speed production line to implement the process changes necessary for the product upgrade; and testing and debugging the production line. The aforementioned efforts may be expensive and time consuming, especially when the reconstruction, testing and debugging steps lead to down time of a high speed production line. Further, when a product upgrade is rolled out on multiple production lines, the time and money required to implement even a small change in each individual line may increase dramatically. Often, the time and money required will be prohibitive, and highly desirable product upgrades may be delayed or even eliminated.

In an attempt to facilitate faster installation, servicing, and adjustment of the working devices, some converting lines may include modular sections joined together. However, such converting lines do not account for difficulties in shipping and require modules to plug into mezzanine type accessory ducts permanently installed. Thus, a converting line configuration that allows for relatively fast and easy product development, relatively low cost and efficient shipping, and reconfiguration is desired, which also minimizes down time due to testing and debugging a production converting line after construction or reconstruction.

SUMMARY OF THE INVENTION

The present disclosure relates to converting lines for manufacturing absorbent articles. The converting lines include a plurality of process equipment converting modules connected with each other along a machine direction (MD). Adjacent converting modules may be releasably connectable to each other with converting module couplers. The converting modules may also have substantially identical dimensions, wherein each converting module defines the same or substantially the same MD length, CD width, and height. The converting modules may also be sized to be received within a standard shipping container. The converting lines may includes a plurality of accessory service modules supported by respective converting modules and connected with each other along the machine directions. The accessory service modules may also be adapted to be received within standard shipping containers. Adjacent accessory service modules may be releasably connected to each other with accessory module couplers, which may include quick-disconnect couplers.

In one form, an apparatus for fabricating disposable absorbent articles includes: a first converting module, a second converting module, and a third converting module, each converting module including a first wall and a second wall separated by a base and a top and defining an interior space, and wherein the each converting module defines a MD length, a CD width, and a height, and wherein each converting module is adapted to be arranged inside a shipping container, wherein the MD length of the converting module extending along an interior width of the shipping container, wherein the interior width of the shipping container is about 2350 mm; a plurality of converting module couplers, the converting module couplers releasably connecting first converting module with the second converting module and releasably connecting the second converting module with the third converting module; a first accessory service module, a second accessory service module, and a third accessory service module, each accessory service module comprising at least one utility duct selected from the group consisting of: a compressed air header duct, a vacuum air header duct, and an electrical power distribution bus duct, and wherein each accessory service module defines a MD length equal to or less than the MD length of each of the converting modules; a plurality of accessory service module couplers comprising at least one quick-disconnect coupler selected from the group consisting of: bus-splice joint plate, flange pull ring locking collars, push-lock couplers, sliding sleeve couplers, cam and groove locking couplers, and flexible pipe hose clamps, the accessory service module couplers releasably connecting the first accessory service module with second accessory service module and connecting the second accessory service module with the third accessory service module; wherein the first accessory module is supported by the first converting module such that the combination of the first accessory module and the first converting module defines a MD length equal to the MD length of the first converting module, wherein the second accessory module is supported by the second converting module such that the combination of the second accessory module and the second converting module defines a MD length equal to the MD length of the second converting module, and the third accessory module is supported by the third converting module such that the combination of the third accessory module and the third converting module defines a MD length equal to the MD length of the third converting module; wherein the second converting module can be removed without removing the first and third converting modules and without removing the first, second, and third accessory modules such that the second accessory module is supported by the accessory module couplers when the second converting module is removed; and wherein the second accessory module can be removed without removing the first and third accessory modules and without removing the first, second, and third converting modules.

In another form, a system for fabrication of disposable absorbent articles includes: a first converting module, a second converting module, and a third converting module, and wherein each converting module defines a MD length, a CD width, and a height, and wherein the MD lengths of modules are equal to each other, a plurality of converting module couplers, the converting module couplers releasably connecting first converting module with the second converting module and releasably connecting the second converting module with the third converting module; a first accessory service module, a second accessory module, and a third accessory module, each accessory module comprising at least one utility duct selected from the group consisting of: a compressed air header duct, a vacuum air header duct, and an electrical power distribution bus duct, and wherein each accessory service module defines a MD length equal to or less than the MD length of each of the converting modules; a plurality of accessory service module couplers comprising at least one quick-disconnect coupler selected from the group consisting of: bus-splice joint plate, flange pull ring locking collars, push-lock couplers, sliding sleeve couplers, cam and groove locking couplers, and flexible pipe hose clamps, the accessory service module couplers releasably connecting the first accessory service module with second accessory service module and connecting the second accessory service module with the third accessory service module; wherein the first accessory module is supported by the first converting module such that the combination of the first accessory module and the first converting module defines a MD length equal to the MD length of the first converting module, wherein the second accessory module is supported by the second converting module such that the combination of the second accessory module and the second converting module defines a MD length equal to the MD length of the second converting module, and the third accessory module is supported by the third converting module such that the combination of the third accessory module and the third converting module defines a MD length equal to the MD length of the third converting module; wherein the second converting module can be removed without removing the first and third converting modules and without removing the first, second, and third accessory modules such that the second accessory module is supported by the accessory module couplers when the second converting module is removed; and wherein the second accessory module can be removed without removing the first and third accessory modules and without removing the first, second, and third converting modules.

In yet another form, a method for shipping a converting line for fabricating disposable absorbent articles includes the steps of: providing a first converting module, a second converting module, and a third converting module, and wherein each converting module defines a MD length, a CD width, and a height, the second converting module releasably connected with and between the first converting module and the third converting module; providing a first accessory service module supported by the first converting module, a second accessory module supported by the second converting module, and a third accessory module supported by the third converting module; disconnecting the second converting module from the first converting module and the third converting module; removing the second converting module from between the first converting module and the third converting module; and supporting the second accessory service module from the first accessory service module and the third accessory service module.

DETAILED DESCRIPTION OF THE INVENTION

Figure 1:
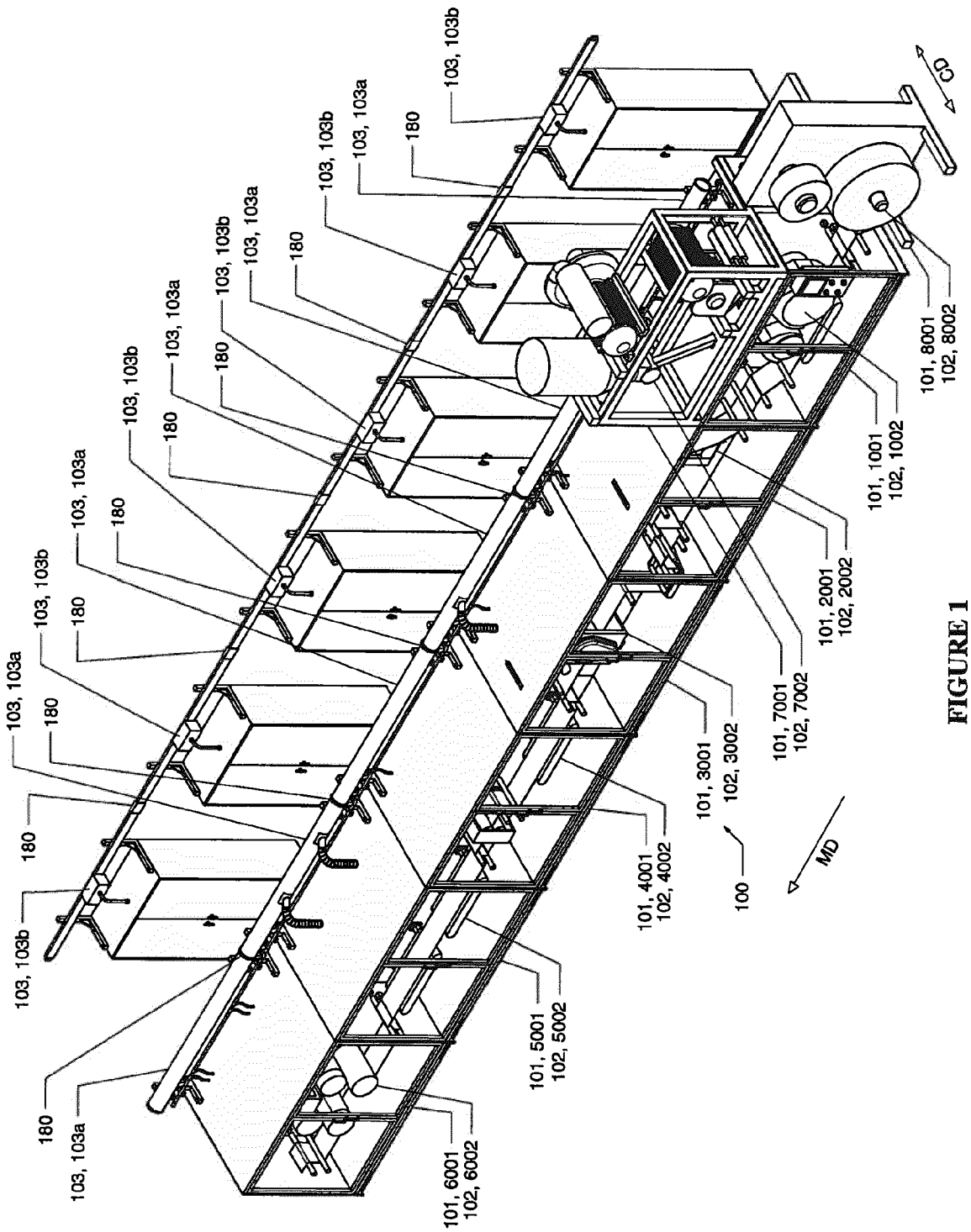
FIG. 1 is a front perspective view of an embodiment of a converting line.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "disposed" is used herein to mean that an element (s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a layer or layers or fibrous materials, films and foils such as plastic films or metallic foils that may be used alone or laminated to one or more web, layer, film and/or foil. As such, a web is a substrate.

The term "nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern.

The term "machine direction" (MD) is used herein to refer to the direction of material flow through a process. The term "cross direction" (CD) is used herein to refer to a direction that is generally perpendicular to the machine direction.

The present disclosure relates to converting lines for manufacturing absorbent articles. An absorbent article converting line may include a combination of converting mechanisms that move substrates and component materials through a manufacturing process. While advancing in the machine direction MD through the converting line, substrates may be combined with the other substrates and/or discrete components to create a continuous length of absorbent articles. Various substrates can be used to construct various components of the absorbent articles, such as backsheets, topsheets, and absorbent cores. Exemplary descriptions of absorbent articles and components are provided in U.S. Pat. Nos. 3,860,003; 5,151,092; 5,554,145; 5,569,234; 5,580,411; and 6,004,306, which are all incorporated by reference herein. At a downstream portion of the converting process, the continuous length of absorbent articles may be subjected to a final knife and cut to create separate and discrete absorbent articles. In addition, defective articles may be removed from the process by a rejection system. Articles that are not deemed to be defective may be subject to further processing steps, such as folding and packaging.

The converting lines herein each include a plurality of process equipment converting modules connected with each other along a machine direction (MD). Each converting module defines an interior space and may house an absorbent article converting mechanism therein. Adjacent converting modules may be releasably connectable to each other with converting module couplers. The converting modules may also have substantially identical dimensions, wherein each converting module defines the same or substantially the same MD length, CD width, and height. As discussed in more detail below, the converting modules may be sized to be received within a standard shipping container. For example, the converting module MD length may be configured to be slightly less than a standard shipping container interior width, and the converting module height may be configured to be slightly less than a standard shipping container interior height. In addition to the aforementioned converting modules, the converting line also includes a plurality of accessory service modules supported by respective converting modules and connected with each other along the machine directions. The accessory service modules may include various ducts and provide access to service utilities, such as electricity, vacuum, and compressed air, to the converting mechanisms. As discussed below, the accessory service modules may also define MD lengths that are the same or substantially the same as the MD lengths of the converting service ducts, and as such, may also be adapted to be received within standard shipping containers. Adjacent accessory service modules may be releasably connected to each other with accessory module couplers, which may include quick-disconnect couplers.

Although the present disclosure is provided in the context of manufacturing absorbent articles, and diapers in particular, it is to be appreciated that the systems and methods disclosed herein may be applied to converting lines used to manufacture of various types of articles and products. Examples of other products include absorbent articles for inanimate surfaces such as consumer products whose primary function is to absorb and retain soils and wastes that may be solid or liquid and which are removed from inanimate surfaces such as floors, objects, furniture and the like. Non-limiting examples of absorbent articles for inanimate surfaces include dusting sheets such as the SWIFFER cleaning sheets, pre-moistened wipes or pads such as the SWIFFER WET pre-moistened cloths, paper towels such as the BOUNTY paper towels, dryer sheets such as the BOUNCE dryer sheets and dry-cleaning clothes such as the DRYEL cleaning clothes all sold by The Procter & Gamble Company. Additional examples of products include absorbent articles for animate surfaces whose primary function is to absorb and contain body exudates and, more specifically, devices which are placed against or in proximity to the body of the user to absorb and contain the various exudates discharged from the body. Non-limiting examples of incontinent absorbent articles include diapers such as PAMPERS diapers, training and pull-on pants such as PAMPERS FEEL 'N LEARN and EASY UPS, adult incontinence briefs and undergarments such as ATTENDS adult incontinence garments, feminine hygiene garments such as panty liners, absorbent inserts, and the like such as ALWAYS and TAMPAX, toilet paper such as CHARMIN toilet paper, tissue paper such as PUFFS tissue paper, facial wipes or clothes such as OLAY DAILY FACIAL wipes or clothes, toilet training wipes such as KANDOO pre-moistened wipes, all sold by The Procter & Gamble Company. Still other examples of products include packaging components and substrates and/or containers for laundry detergent and coffee, which may be produced in pellets or pouches and may be manufactured in a converting or web process or even discreet products produced at high speed such as high-speed bottling lines, cosmetics, razor blade cartridges, and disposable consumer batteries.

Figure 2:
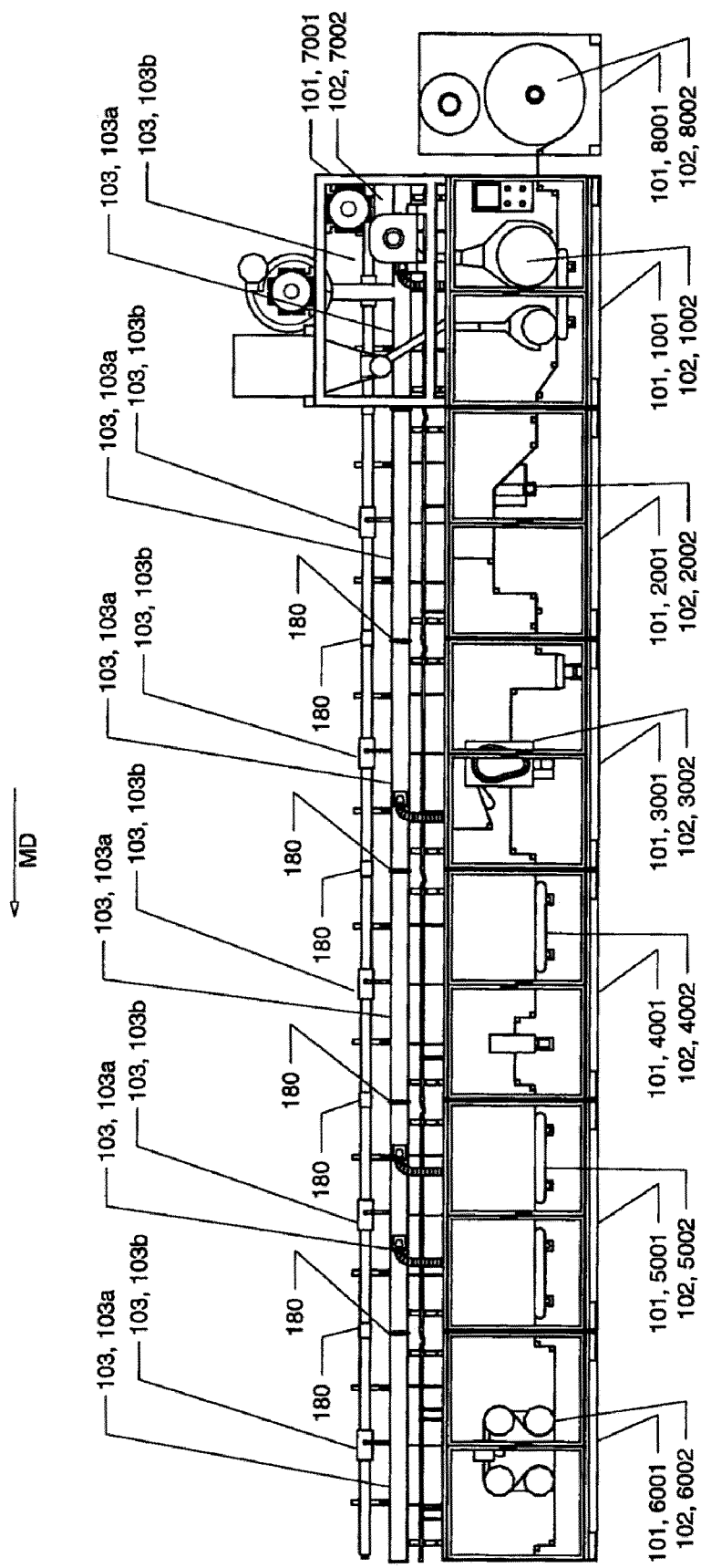
FIG. 2 is a front side view of the converting line of FIG. 1 showing schematic representations of converting mechanisms housed within the converting modules.

FIGS. 1 and 2 show an embodiment of a converting line 100 including a plurality of process equipment converting modules 101 arranged along a machine direction MD. As shown, seven converting modules 101 are positioned on a floor with one converting module 101 one stacked on top of another. Although the converting line 100 includes seven converting modules 101, it is to be appreciated that other embodiments may include more or less than seven converting modules. As discussed in more detail below, the converting modules 101 are releasably connected to each other and may be configured with substantially the same dimensional features. The converting modules 101 may also house and/or support a converting mechanism 102. The converting mechanisms 102 may be configured to perform various different manufacturing functions along the converting line 100. The converting line shown in FIGS. 1 and 2 also includes a plurality of accessory service modules 103 arranged along the machine direction. The accessory service modules 103 provide access to various utilities to the converting modules 101 and/or converting mechanisms 102 and are releasably connected with each other. As discussed below, the accessory service modules 103 are supported by corresponding converting modules 101 and/or by adjacent accessory service modules 103.

Figure 3:
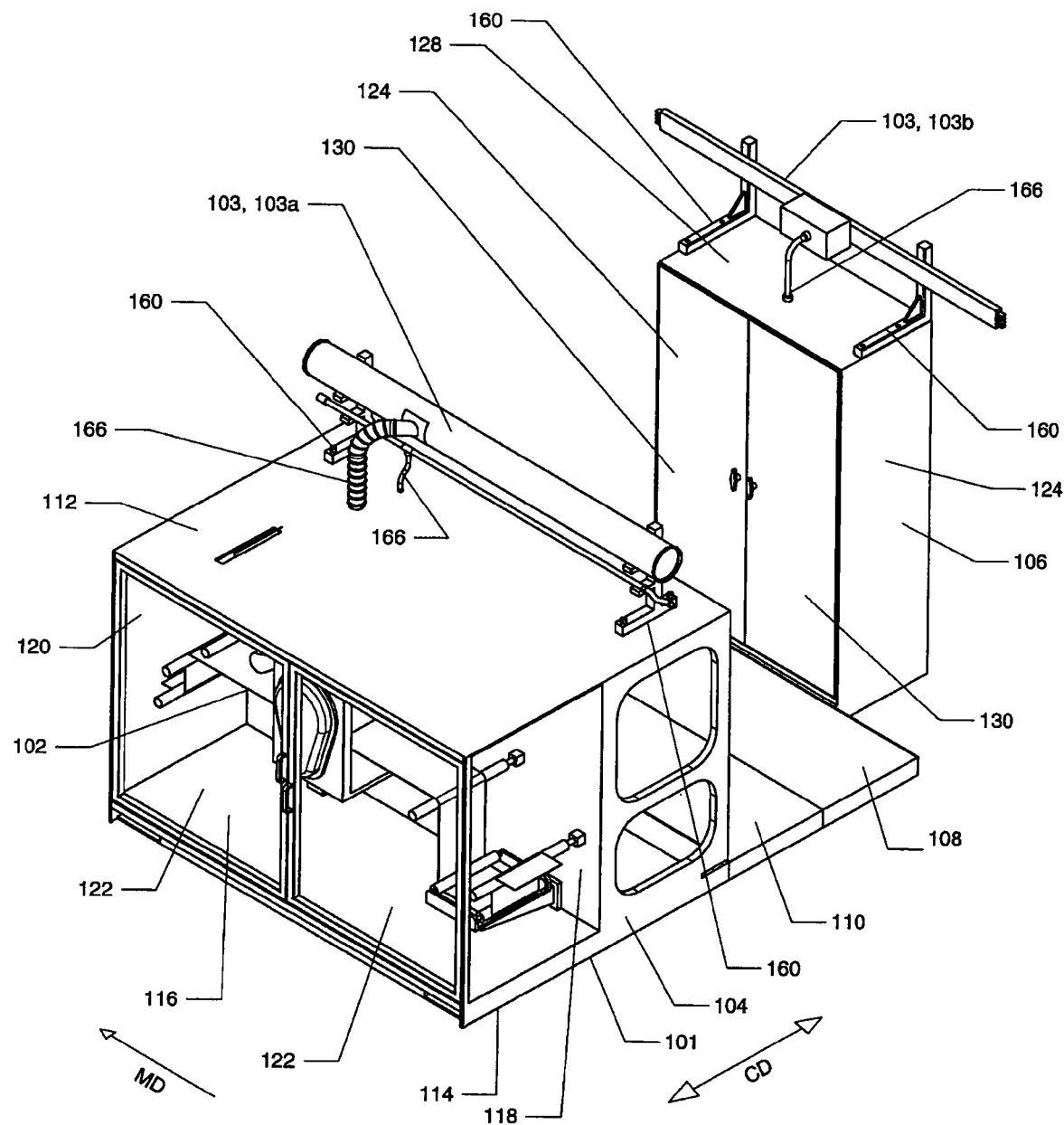
FIG. 3 is a detailed perspective view of a converting module and associated accessory service modules from the converting line of FIG. 1.
Figure 4:
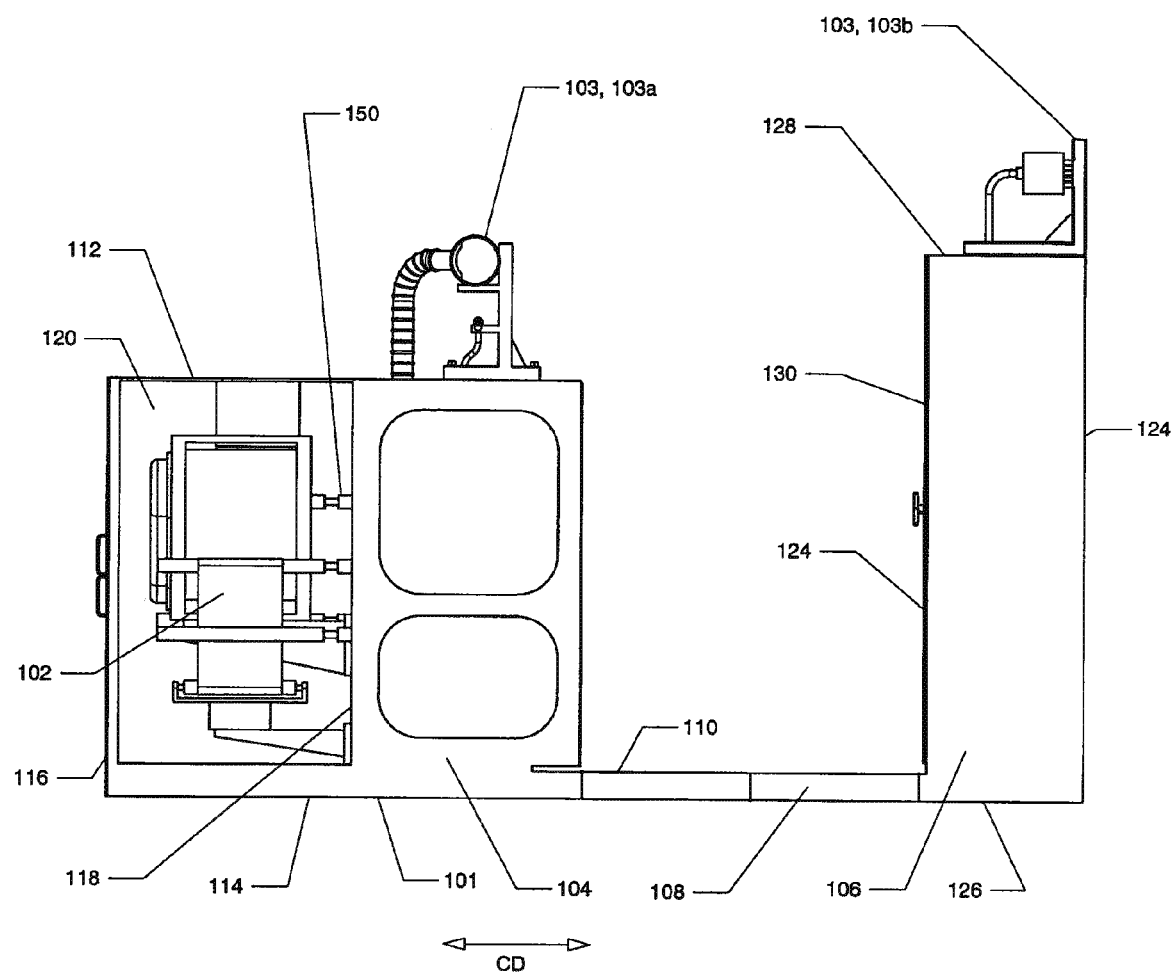
FIG. 4 is a right side view of the converting module and accessory service modules of FIG. 3.
Figure 10:
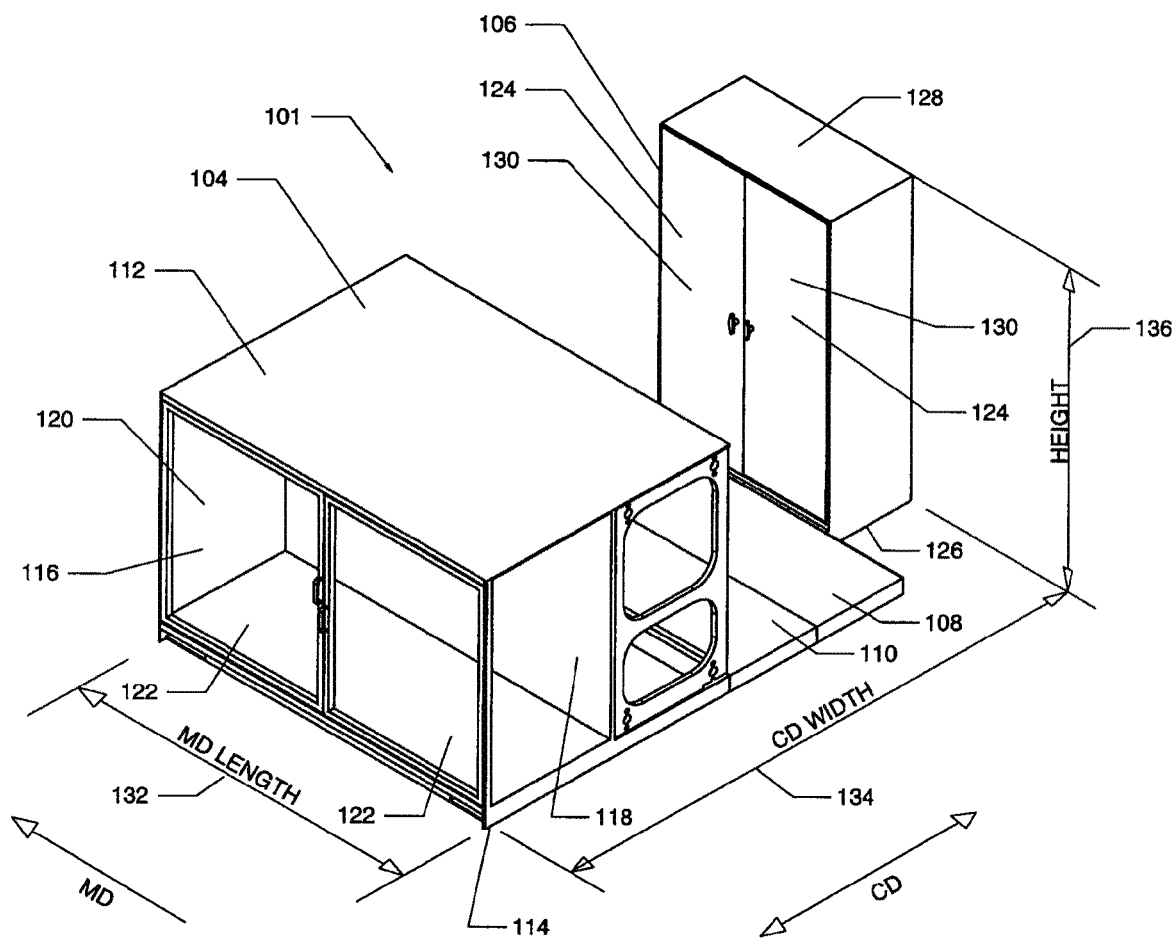
FIG. 10 is a perspective view of a converting module.

FIGS. 3 and 4 show an embodiment of a converting module 101 supporting two accessory service modules 103, and FIG. 10 shows the converting module 101 with the accessory service modules 103 removed. As shown, the converting module 101 may include a converting cabinet 104 and a controller cabinet 106. The converting cabinet supports a first accessory service module 103a, and the controller cabinet 106 supports a second accessory service module 103b. A cable tray 108 connects the converting cabinet 104 with the controller cabinet 106. As discussed in more detail below, the cable tray 108 may also function as a walkway 110 and may be selectively configurable to reduce the CD width of the converting module 101.

With reference to FIGS. 3, 4, and 10, the converting cabinet 106 includes a top 112 and a base 114 separated by a first wall 116 and a second wall 118. An interior space 120 is defined by between the first wall 116, the second wall 118, the top 112, and the base 114. As discussed in more detail below, a converting mechanism 102 may be disposed in the interior space 120. Portions of the converting mechanism 102 may be supported by the second wall 118 and/or the base 114 of the converting cabinet 104. In addition, the first wall 116 may include doors having transparent panels to enable access and viewing of the interior space 120 of the converting cabinet 104. The controller cabinet 106 may include four walls 124 connected with and separating a base side 126 from a top side 128. The controller cabinet 106 may be configured to house various items, such as motor control modules, which may in turn, be connected with the converting mechanism 102 with cables. Such cables may be routed from the controller cabinet 106 to the converting cabinet 104 through the cable tray 108. The controller cabinet 106 may also include one or more doors 130 to provide access to the items housed within the controller cabinet 106.

As shown in FIG. 10, the converting module defines a MD length 132, a CD width 134, and a maximum height 136. With the converting module 101 embodiment shown in FIG. 10, the height of the controller cabinet 106 is greater than the height of the converting cabinet 104, and thus, the controller cabinet 106 defines the maximum height 136 of the converting module 101. It is to be appreciated that in other embodiments, the height of the converting cabinet 104 may be the same or greater than the height of the controller cabinet 106. It should also be appreciated that the converting modules 101 may be configured to have various ranges of MD lengths, CD widths, and heights. For example, in one embodiment, the converting line 100 may include converting modules 101 having MD lengths 132 of less than or equal to 2200 mm, CD widths 134 of less than or equal to 3570 mm, and/or heights 136 of less than or equal to 2275 mm.

Figure 5:
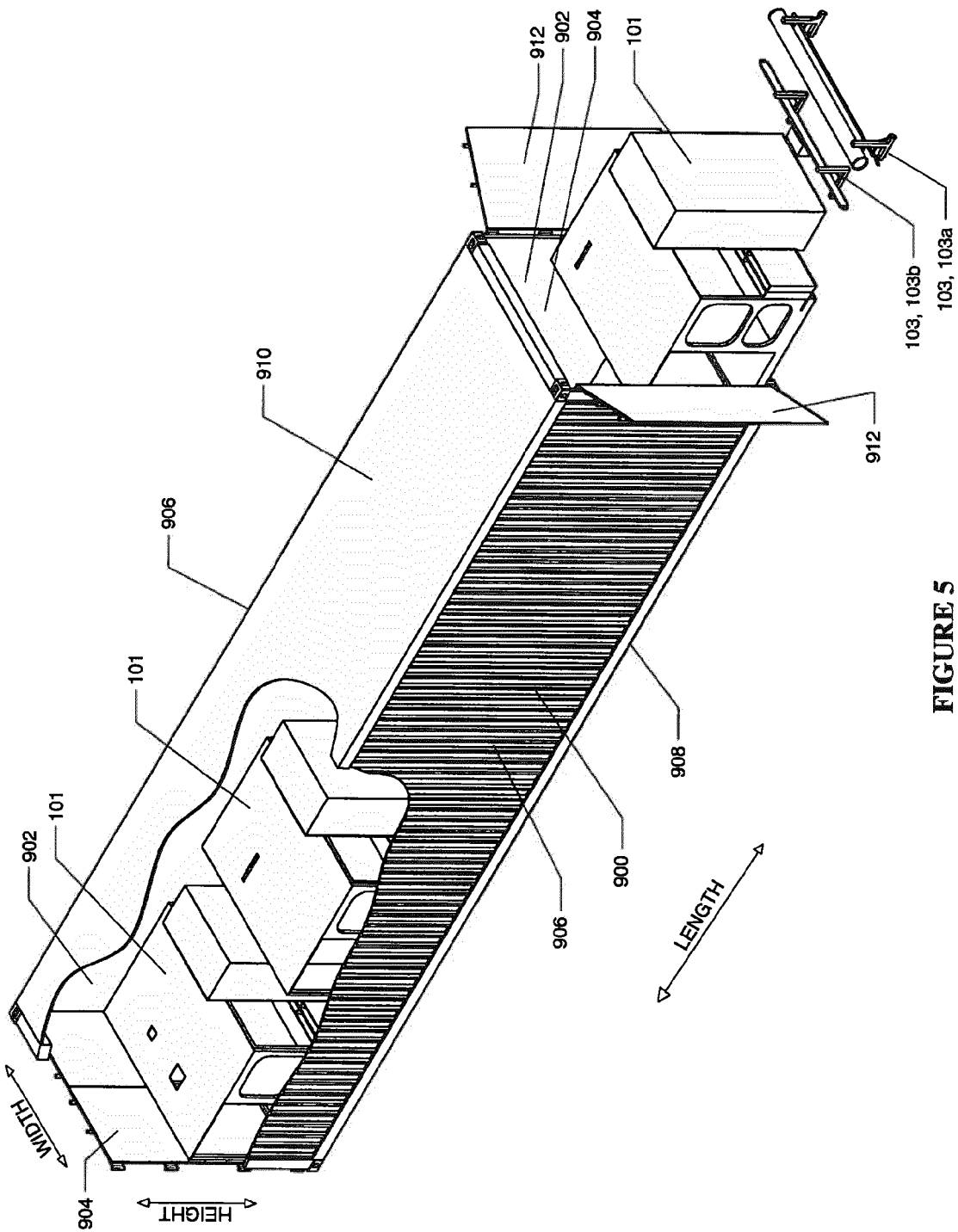
FIG. 5 is an overall perspective view of converting modules and accessory service modules being arranged inside a standard shipping container.

In some embodiments, the converting modules 101 are sized to fit inside standard shipping containers. Shipping containers may also be provided in various sizes and shapes. In some instances, in order to avoid having to produce and/or purchase customized shipping containers, vendors may offer customers "standard" sized shipping containers within which to house articles to be transported and/or stored. For example, FIG. 5 shows an example of a standard sized "high cube" shipping container 900 available from some vendors. The shipping container 900 may include an interior space defined by two relatively short sides 902, two relatively long sides 904, a bottom side 906, and a top side 908. As such, the shipping container defines an interior width between the two long sides 904, an interior length between the short sides 902, and an interior height between the top side 908 and bottom side 906. One or more of the sides of the shipping container may include one or more doors 912 for access to the interior space 902. In one embodiment, the shipping container 900 may have an interior length of about 12030 mm, an interior width of about 2350 mm, and an interior height of about 2700 mm.

FIG. 5 also shows embodiments of converting modules 101 sized to be received within the shipping container 900. In particular, portions of the top side 910 and a long side 906 are partially cut-away in FIG. 5 to illustrate two converting modules 101 located within the interior space 902 of the shipping container 900. A converting module 101 is also illustrated as partially inserted into the shipping container 900 through the short side 904 having two doors 912. The converting modules 101 are configured to be received within the shipping container 900 such that the MD lengths 132 of the converting modules 101 extend along the interior width of the shipping container 900, and the CD widths 134 of the converting modules 101 extend along the interior length of the shipping container 900. The converting module 101 may define a MD length 132 that is slightly less than the interior width of the shipping container 900. The converting module may also define a maximum height 136 that is less than the interior height of the shipping container 900 and may define a CD width 134 that is less than interior length of the shipping container. In some instances, the CD width 134 of the converting modules 101 may be substantially less than the interior length of the shipping container 900, and as such, a plurality of the converting modules 101 can be arranged adjacent to each other along the interior length of the shipping container 900. In one embodiment, five converting modules 101 can be received within one standard 40 foot long, "high cube" shipping container.

Figure 6B:
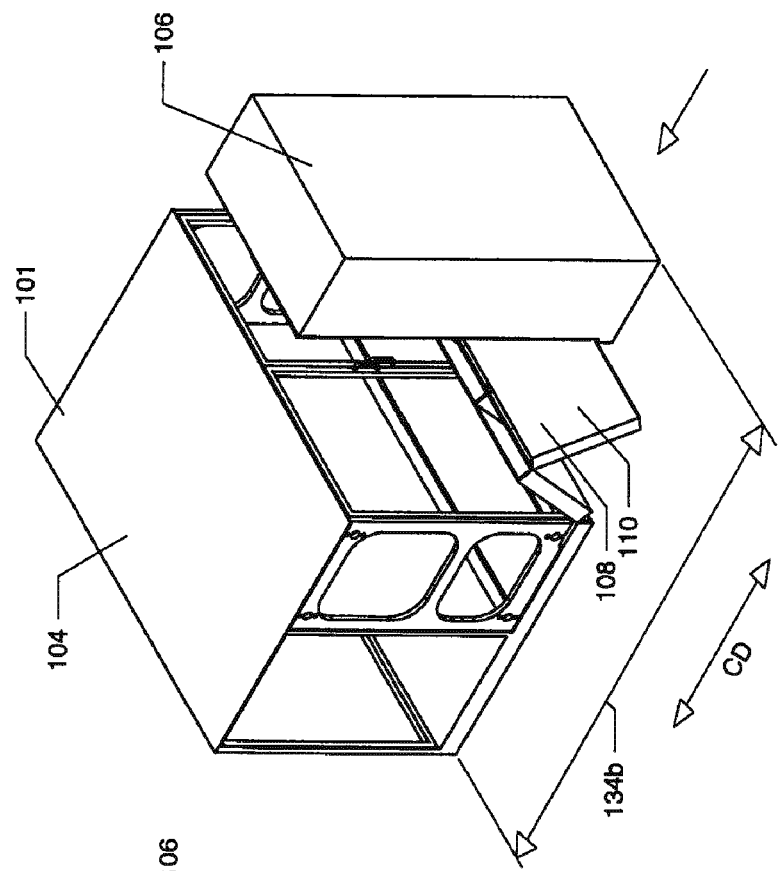
FIG. 6B is a detailed perspective view of the converting module of FIG. 6A showing the cable tray being placed in a folded position.
Figure 6A:
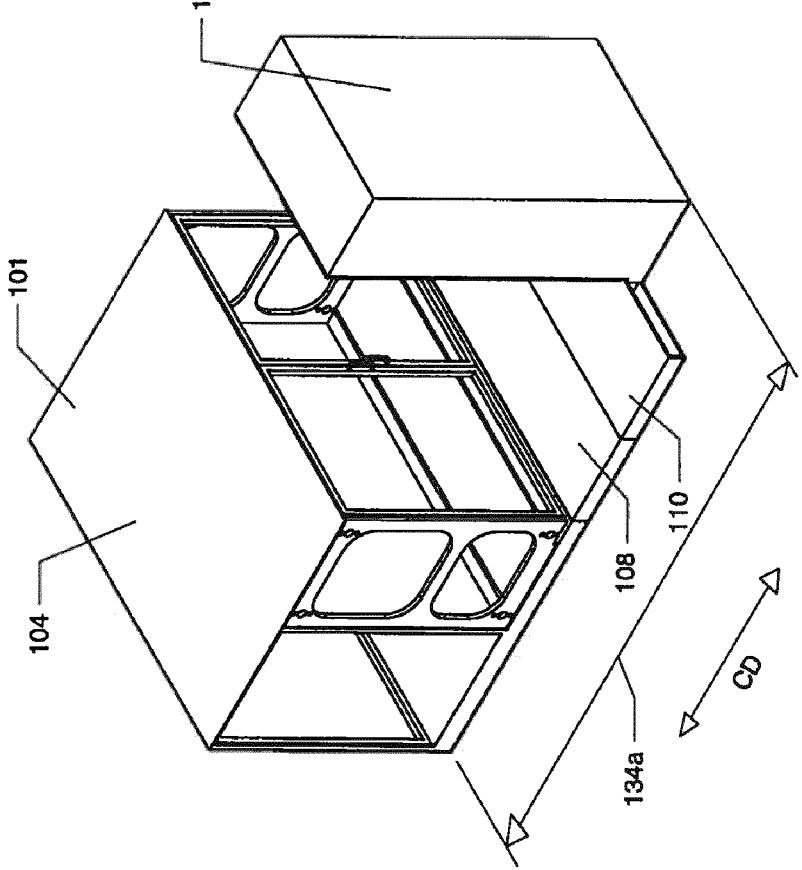
FIG. 6A is a detailed perspective view of a converting module including a foldable cable tray.
Figure 6D:
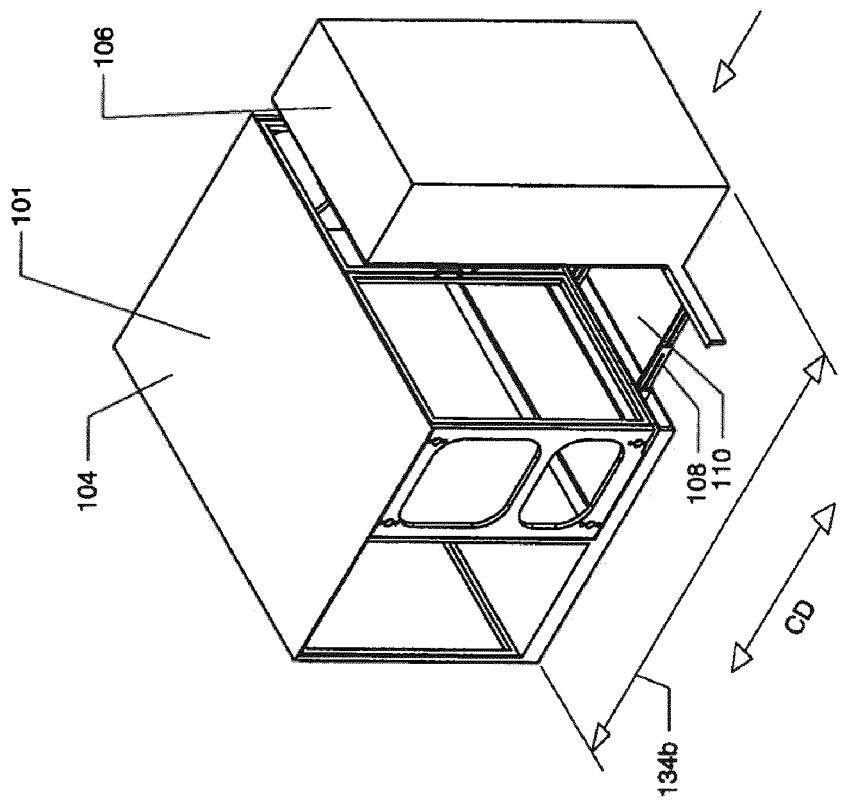
FIG. 6D is a detailed perspective view of the converting module of FIG. 6D showing the cable tray being placed in a contracted position.
Figure 6C:
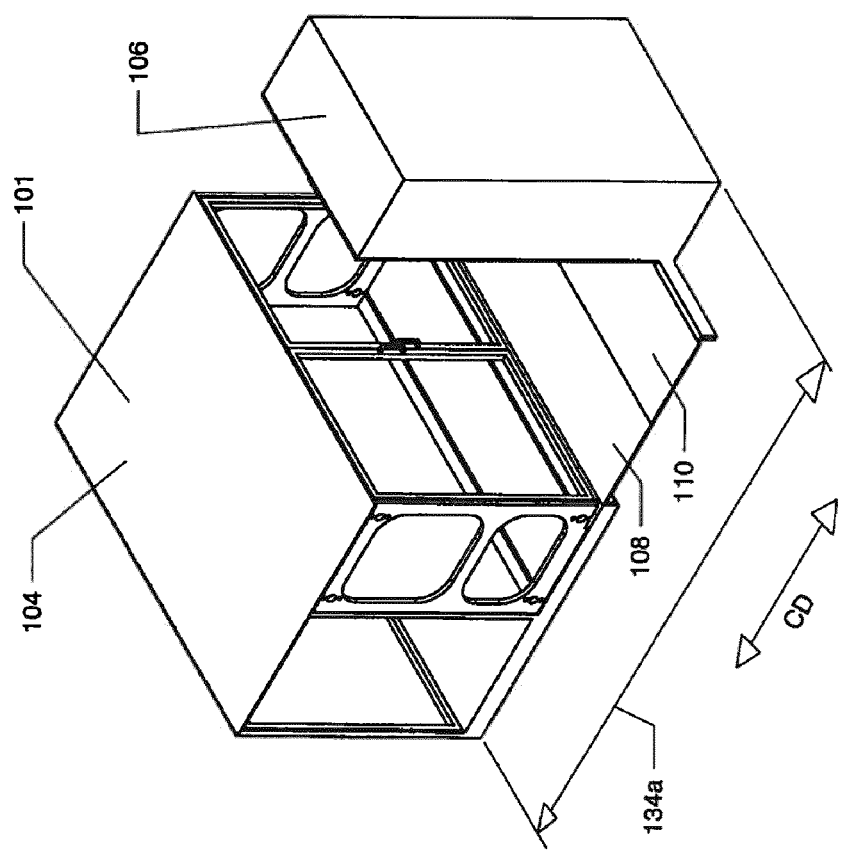
FIG. 6C is a detailed perspective view of a converting module including a telescoping cable tray.

To help reduce the space needed when shipping converting modules 101, the converting modules 101 may include cable trays 108 that are selectively positionable. In particular, the cable tray 108 may be configurable between a first position and a second position to selectively adjust the CD width 134 of the converting module 101. As such, the converting module may define a first CD width when the cable tray is in the first position, and the converting module may define a second CD width when the cable tray is in the second position, wherein the second CD width is less than the first CD width. In one example, such as shown in FIGS. 6A and 6B, the converting module may include a walkway 110 and/or cable tray 108 that is foldable. FIG. 6A shows the cable tray 108 in a first, extended position, wherein the converting module 101 defines a first CD width 134a. FIG. 6B shows the cable tray being placed in a second, folded position, wherein the converting cabinet 104 and controller cabinet 106 are placed in closer proximity to each other such that the converting module 101 defines a second CD width 134b that is less than the first CD width 134a. In another example, such as shown in FIGS. 6C and 6D, the converting module 101 may include walkway 110 and/or cable tray 108 that is telescopically connected between the converting cabinet 104 and the controller cabinet 106. FIG. 6C shows the cable tray 108 in a first, extended position, wherein the converting module 101 defines a first CD width 134a. FIG. 6D shows the cable tray 108 being placed in a second, retracted position, the converting cabinet 104 and controller cabinet 106 are placed in closer proximity to each other such that the converting module 101 defines a second CD width 134b that is less than the first CD width 134a. It is to be appreciated that the second CD width 134b can be configured to have various lengths. For example, in one embodiment the second CD width 134b is 2400 mm.

Figure 7:
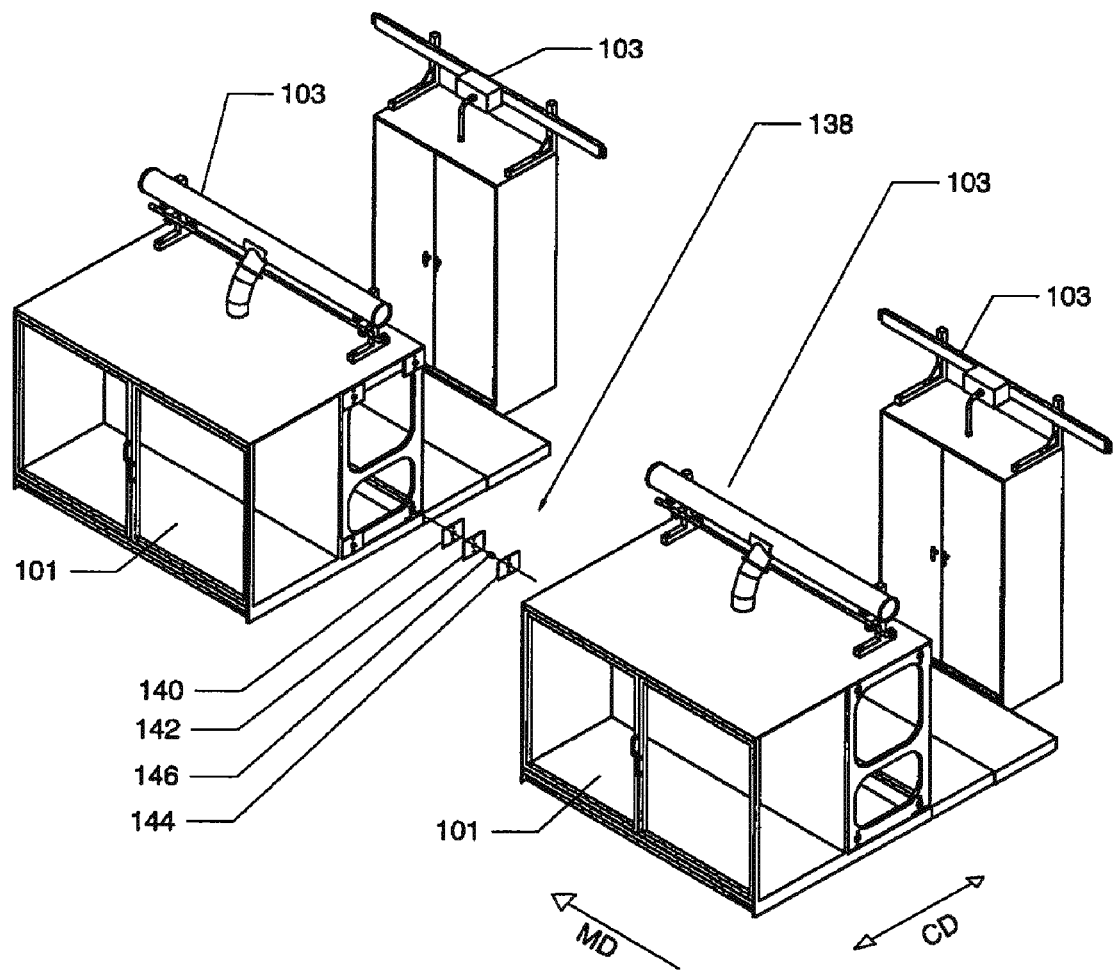
FIG. 7 is an exploded view of a converting module coupler arranged to connect two converting modules together.
Figure 8:
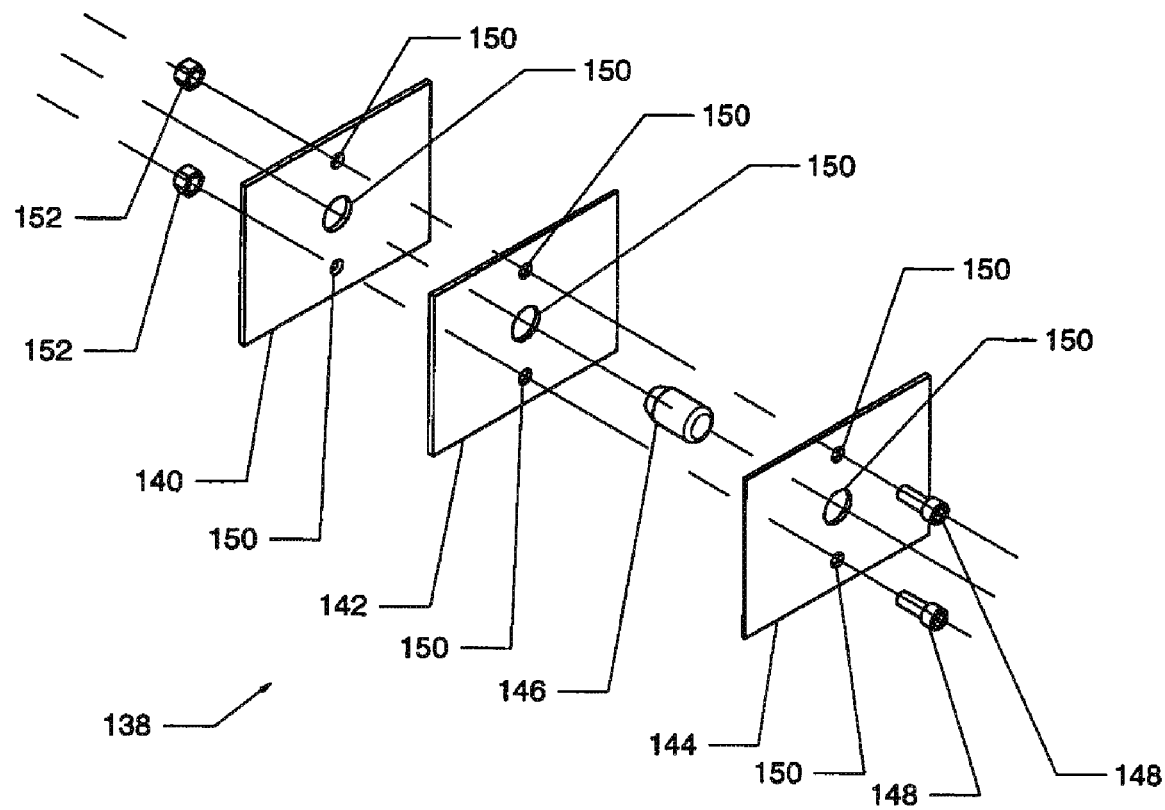
FIG. 8 is a detailed exploded perspective view of a converting module coupler shown in FIG. 7.
Figure 9:
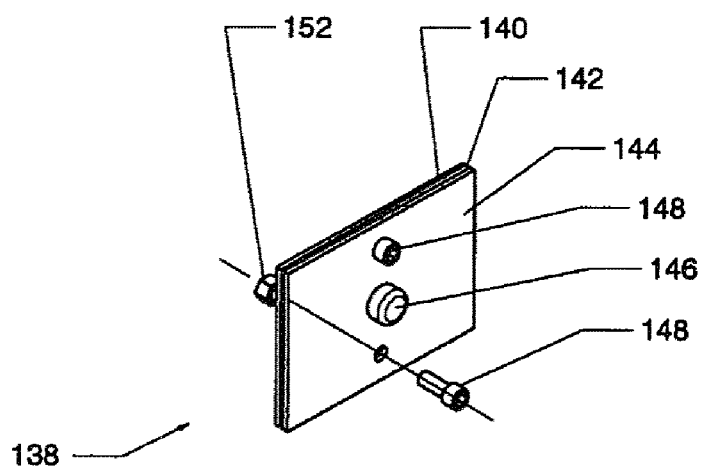
FIG. 9 is a detailed assembly view of the converting module coupler of FIG. 8.

As previously mentioned, the converting modules 101 may be releasably connected with adjacent converting modules 101 along the machine direction MD. For example, FIG. 7 shows a converting module coupler 138 for releasably connecting two converting modules 101 with each other. FIGS. 8 and 9 show detailed views of one embodiment of the converting module coupler 138. With reference to FIGS. 7-9, when connecting two converting modules 101 together, one converting module 101 is place adjacent to another converting module 101 with a space or gap between the converting modules along the MD direction. In one embodiment, the space may be 20 mm. A spacer or a set of complimentary wedges 140, 142, 144 may be inserted between the converting modules 101 in the MD gap or space provided. A pin 146 and two bolts 148 may be inserted through holes 150 in the spacer or wedges 140, 142, 144 and corresponding holes in the adjacent converting modules 101. The bolts 148 may be joined with nuts 152 to provide a tight connection between the converting modules 101. It is to be appreciated that one, two, three, or four sets of spacers or wedges with pins and bolts can be used to releasably connect the converting modules 101 to provide a desired spacing, alignment, and connection. It is also to be appreciated that other types of converting module couplers 138 may be used to provide for connection and alignment as well as releasably connect the converting modules 101 together.

As previously mentioned, the converting modules 101 may house various types of converting mechanisms 102. For example, the configuration shown in FIGS. 1 and 2 illustrates a converting line 100 including eight converting modules 101 housing eight corresponding converting mechanisms 102, which in combination, are adapted to produce a disposable absorbent article in the form of a diaper. Each converting mechanism 102 may be configured to perform various functions of the converting process as materials advance in the machine direction MD through the converting line 100. The following provides a general description of various converting mechanism arrangements that may be utilized with the converting line 100.

With reference to FIGS. 1 and 2, in one embodiment, the converting line may 100 include a first converting module 1001 housing a first converting mechanism 1002 in the converting cabinet 104. The first converting mechanism 1002 may be adapted to create a composite web by forming an absorbent patch and combining the absorbent patch with a topsheet carrier web and a second absorbent patch. The composite web may then advance in the machine direction to a second converting mechanism 2002 housed within a second converting module 2001. The second converting module 2001 is releasably connected with the first converting module 1001. The second converting mechanism 2002 may be adapted to fold a topsheet carrier web around absorbent materials and to add an additional continuous web into the converting process. The composite web may then advance in the machine direction to a third converting mechanism housed within a third converting module 3001. The third converting module 3001 is releasably connected with the second converting module 2001. The third converting mechanism 3002 may be adapted to periodically add a discontinuous thin material onto the web. The composite web may then advance in the machine direction to a fourth converting mechanism 4002 housed within a fourth converting module 4001. The fourth converting module 4001 is releasably connected with the third converting module 3001. The fourth converting mechanism 4002 may be adapted to compress the composite web. The composite web may then advance in the machine direction to a fifth converting mechanism 5002 housed within a fifth converting module 5001. The fifth converting module 5001 is releasably connected with the fourth converting module 4001. The fifth converting mechanism 5002 may be adapted to transport the composite web through the fifth converting module 5001. The composite web may then advance in the machine direction to a sixth converting mechanism 6002 housed within a sixth converting module 6001. The sixth converting module 6001 is releasably connected with the fifth converting module 5001. The sixth converting mechanism 6002 may be adapted to ultrasonically treat the composite web. The composite web may then advance in the machine direction to other converting modules 101 housing other mechanisms and/or to other machinery which may further transform the web or package the assembled products.

The converting line in FIGS. 1 and 2 also includes a seventh converting module 7001 disposed on top of the first converting module 1001. The seventh converting module 7001 may include a seventh converting mechanism 7002 adapted to meter and deliver two forms of particulate absorbent material to the first converting module 1001 from which the absorbent patches are formed. Further, the seventh module 7001 may also support equipment which supplies vacuum to the fluid services header. In addition, the converting line 100 may includes an eighth module 8001 positioned adjacent to and upstream of the first converting module 1001. The eighth module 8001 may include a converting mechanism 8002 adapted to supply a topsheet carrier web to the first converting module 101 and also supply continuous absorbent material to the seventh module 7001 for disintegration into particulate absorbent material.

As discussed above, the converting line 100 includes a plurality of accessory service modules 103 supported by respective converting modules 101. The accessory service modules 103 provide service utilities to the converting modules 101 and/or converting mechanisms 102 housed within the converting modules. It is to be appreciated that the accessory service modules 103 may include more or less and/or different service utilities than are shown and described herein.

Figure 11:
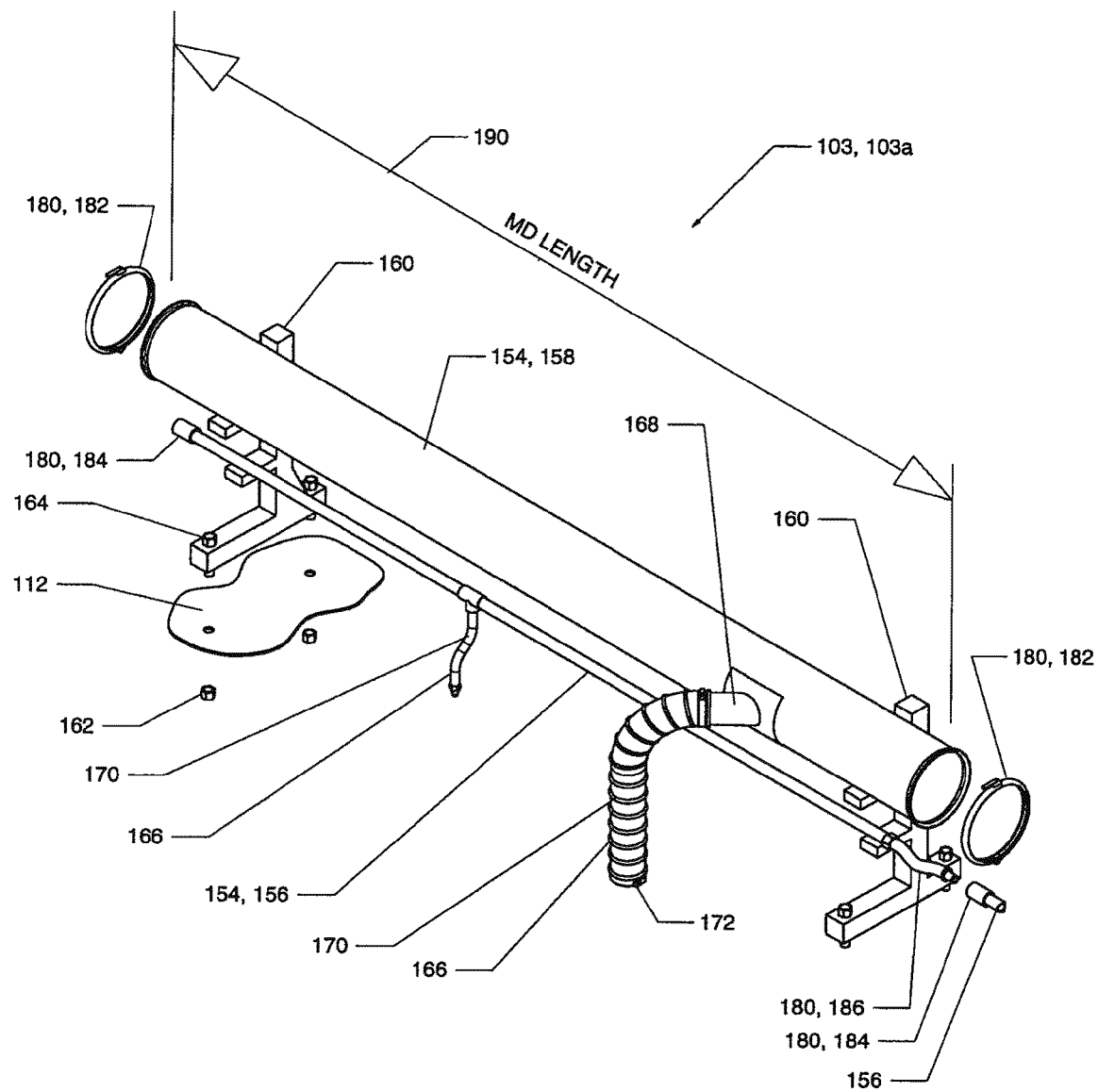
FIG. 11 is a perspective view of a first accessory service module.

For example, FIG. 11 shows a first embodiment of an accessory service module 103a that includes a plurality of accessory service ducts 154, such as for example, a compressed air header duct 156 and a vacuum air header duct 158. The accessory service modules 103 may be supported by corresponding converting modules 101 in various ways. For example, the accessory service module 103a shown in FIG. 11 includes support brackets 160 that can be releasably connected with a corresponding converting module 101. For example, the support brackets 160 shown in FIG. 11 are adapted to connect with the top 112 of a converting cabinet 104, such as shown in FIG. 3. It is to be appreciated that the support brackets can be releasably connected with the converting modules in various ways, such as for example, nuts 162 and bolts 164 or other types of fasteners. The support brackets 160 are also configured to support the accessory service ducts 154 above the top of the converting cabinet 104. The accessory service module 103 may also include duct couplers 166 releasably connecting accessory service ducts 154 with adjacent converting modules 101 and/or converting mechanisms 102 housed therein. It is to be appreciated that duct couplers 166 may be configured in various ways. For example, as shown in FIG. 11, the duct couplers 166 may include rigid pipes 168 and/or flexible hoses 170 as well as releasable connectors 172 such as unions and/or other types of pipe or hose quick disconnects.

Figure 12:
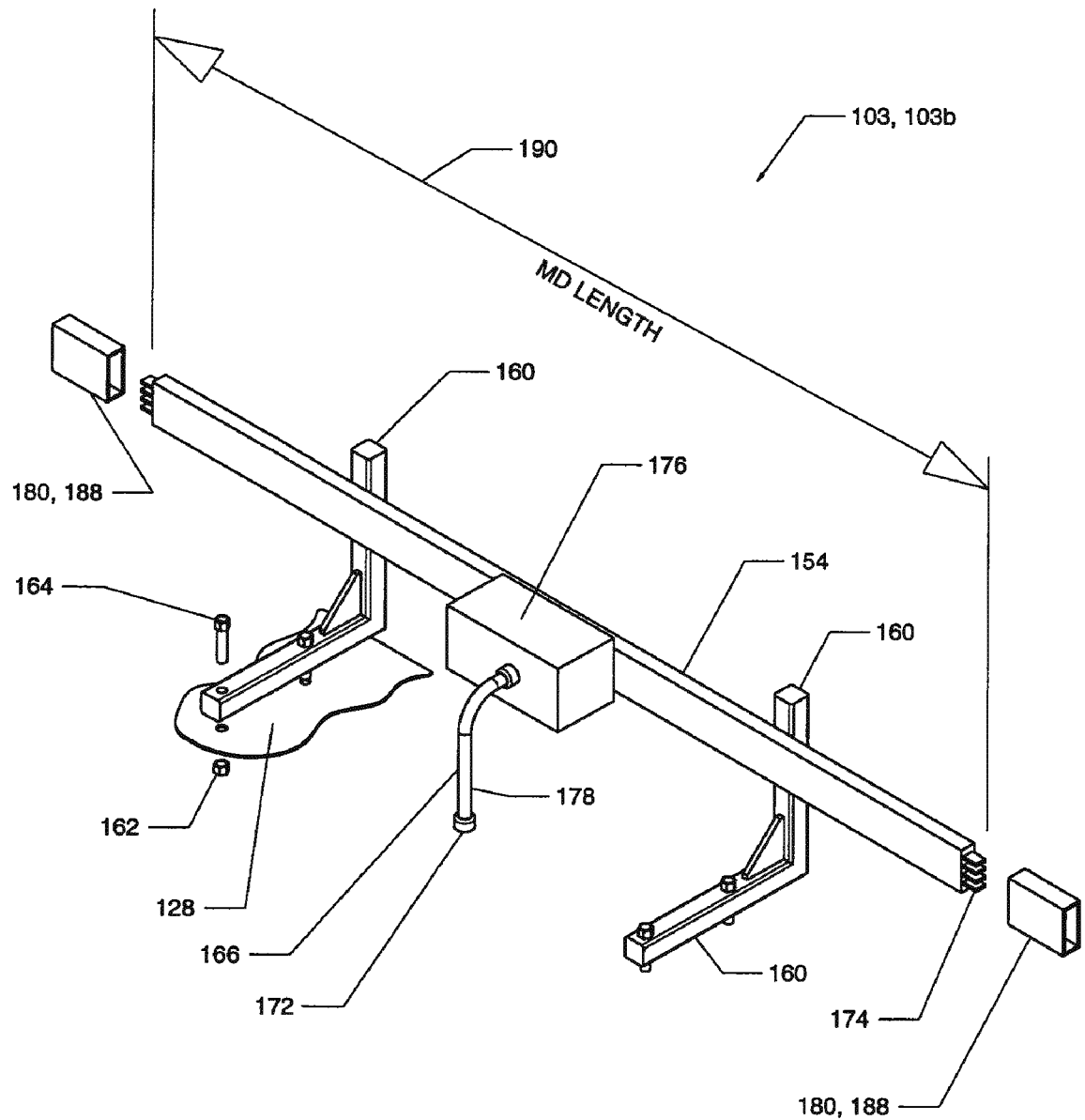
FIG. 12 is a perspective view of a second accessory service module.

A second embodiment of an accessory service module 103b is shown in FIG. 12 that includes an accessory service duct 154 housing an electrical power distribution bus duct 174. The accessory service module 103b shown in FIG. 12 also includes support brackets that can be connected with a corresponding converting module 101. For example, the support brackets 160 shown in FIG. 12 are adapted to connect with the top 128 of a controller cabinet 106, such as shown in FIG. 3. The support brackets 160 can also be releasably connected with the converting modules 101 in various ways, such as for example, nuts 162 and bolts 164 or other types of fasteners. The support brackets 160 are also configured to support the accessory service ducts 154 above the top 128 of the controller cabinet 106. As mentioned above, the accessory service modules 103 may also include various forms of duct couplers 166 to releasably connect accessory service ducts 154 with adjacent converting modules 101 and/or converting mechanisms 102 housed therein. For example, as shown in FIG. 12, the duct couplers 166 may include a junction box 176 and associated rigid and/or flexible conduits 178 as well as releasable connectors 172 such as unions and/or other types of pipe or hose quick disconnects to releasably connect the electrical bus ducts 174 with adjacent converting modules 101. Cables may also releasably connect the electrical power distribution bus ducts with servo motor controller housed within respective controller cabinets.

As discussed above, a plurality of accessory service modules 103 are arranged along the machine direction MD and may be supported by respective converting modules 101. In addition, the accessory service modules 103 may be releasably connected with each other with accessory service module couplers 180. As discussed in more detail below, an accessory service module 103 may be supported by adjacent accessory service modules 103 when a corresponding converting module 101 is removed from the converting line 100. The accessory service module couplers 180 may comprise various forms of quick-disconnect couplers. For example, in one embodiment, the accessory service module couplers 180 may be configured as flange pull ring locking collars 182, such as shown in FIG. 11, to releasably connect adjacent vacuum air header ducts 158. In another example shown in FIG. 11, the accessory service module couplers 180 may be configured as push-lock couplers 184 which may be in combination with flexible piping 186 to connect adjacent compressed air ducts 156. In other embodiments, the accessory service module couplers 180 may comprise, sliding sleeve couplers, cam and groove locking couplers, and flexible pipe hose clamps. In another example, shown in FIG. 12, the accessory service module couplers 180 may include quick-disconnect plugs and bus splice joint plates 188, bus tap or plug-in boxes to releasably connect adjacent electrical power distribution bus ducts 174.

As discussed above with respect to the converting modules 101, the accessory service modules 103 may also be configured to be received within standard shipping containers. As such, the accessory service modules 103 may define MD lengths 190, such as shown in FIGS. 10-12, that are the same as or less than the MD lengths 132 of the converting modules 101. For example, the accessory service modules 103 can be sized to be received within shipping containers 900 such that the MD length 190 of the accessory service module 103 extends along the interior width of a shipping container 900, such as shown in FIG. 5.

Figure 13:
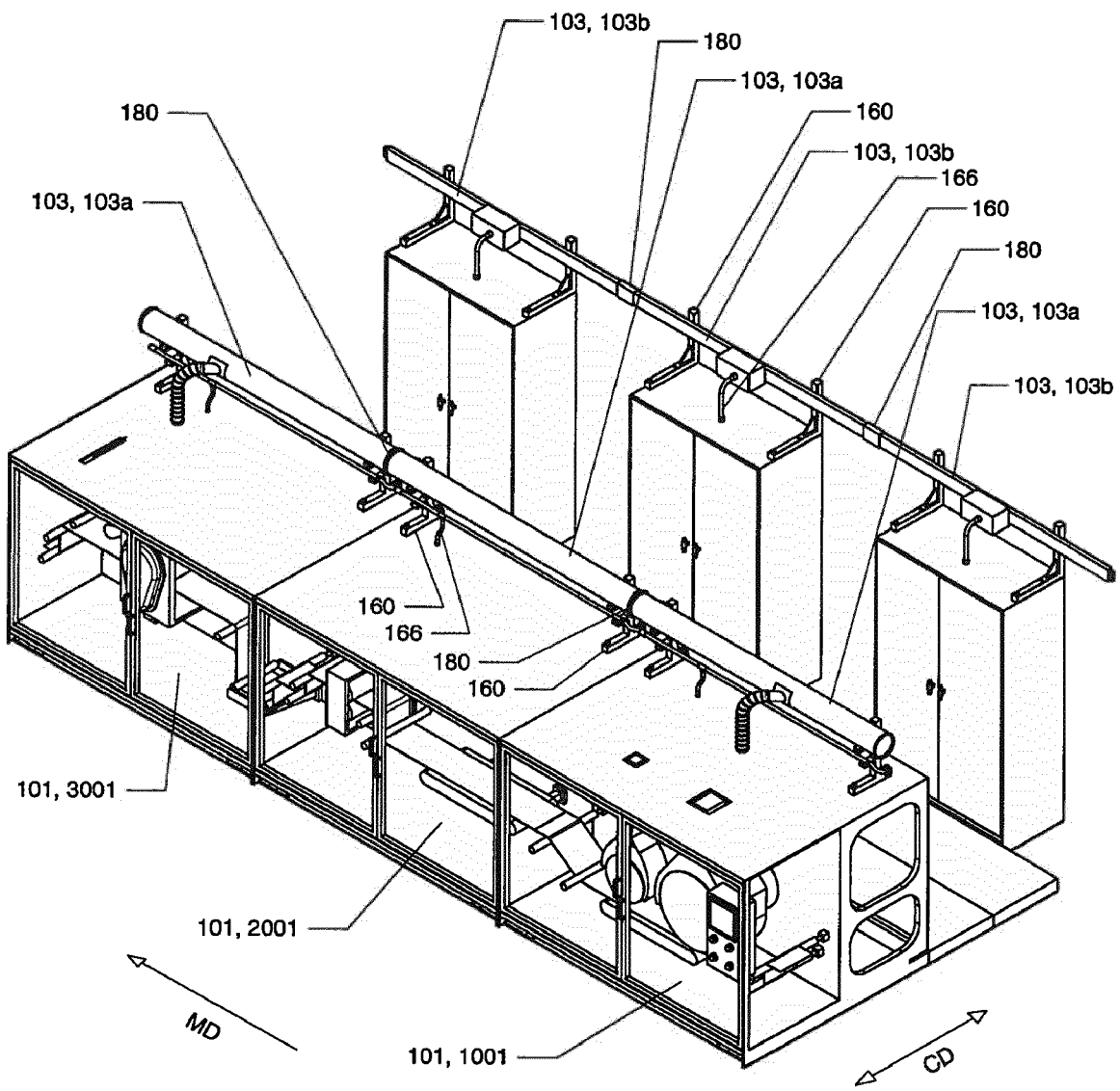
FIG. 13 is a detailed perspective view of three converting modules and accessory service modules from FIG. 1.
Figure 14:
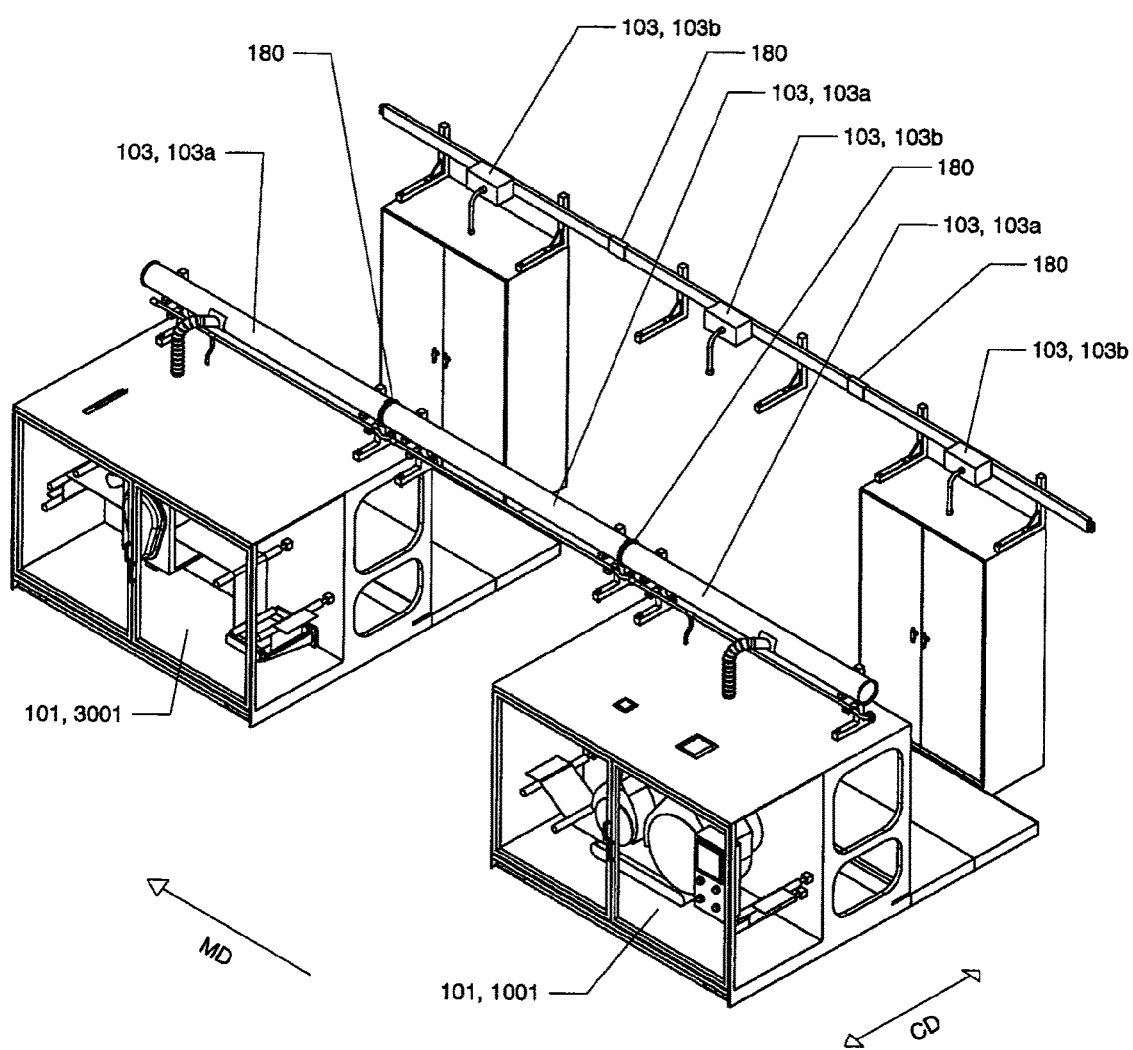
FIG. 14 is a detailed perspective view showing the middle converter module removed from the arrangement shown in FIG. 12.
Figure 15:
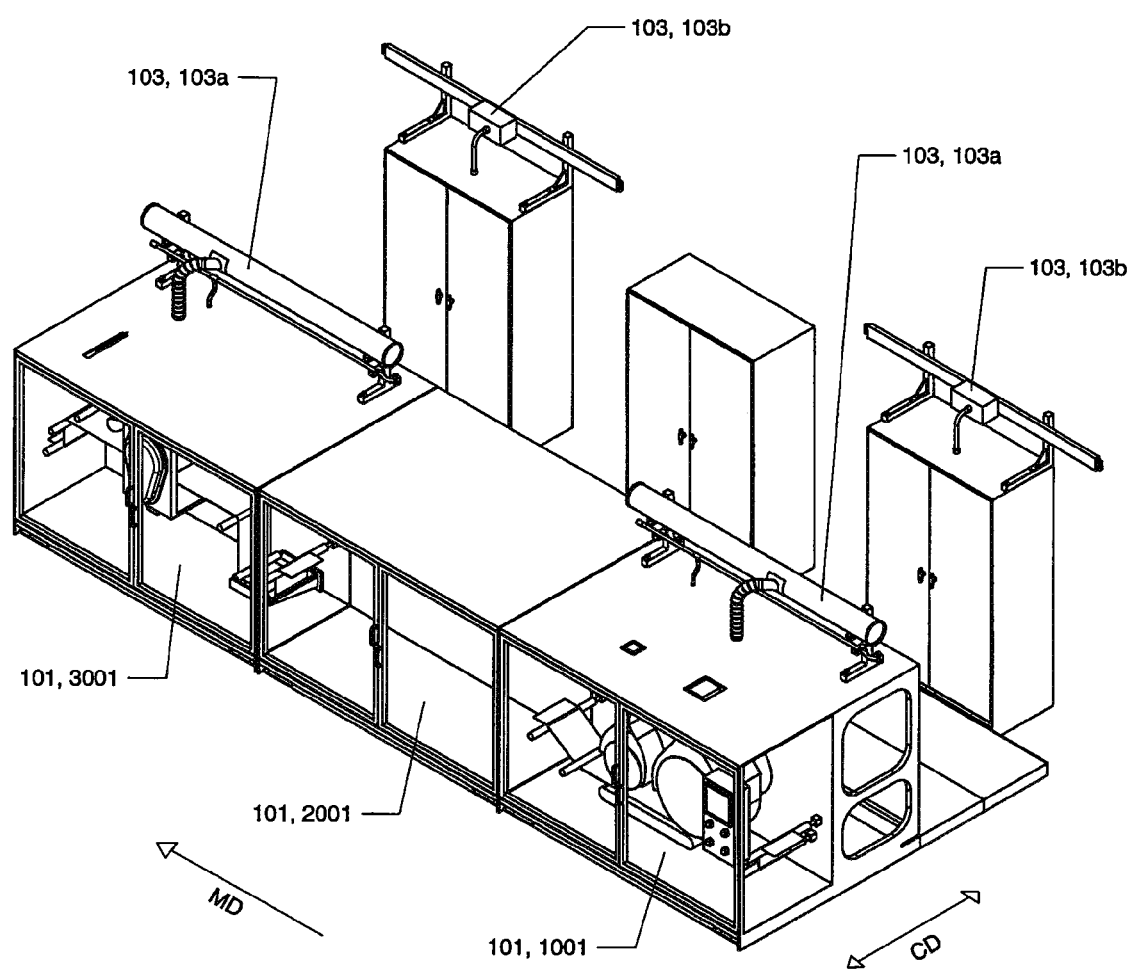
FIG. 15 is a detailed perspective view showing middle accessory service modules removed from the arrangement shown FIG. 12.
Figure 16:
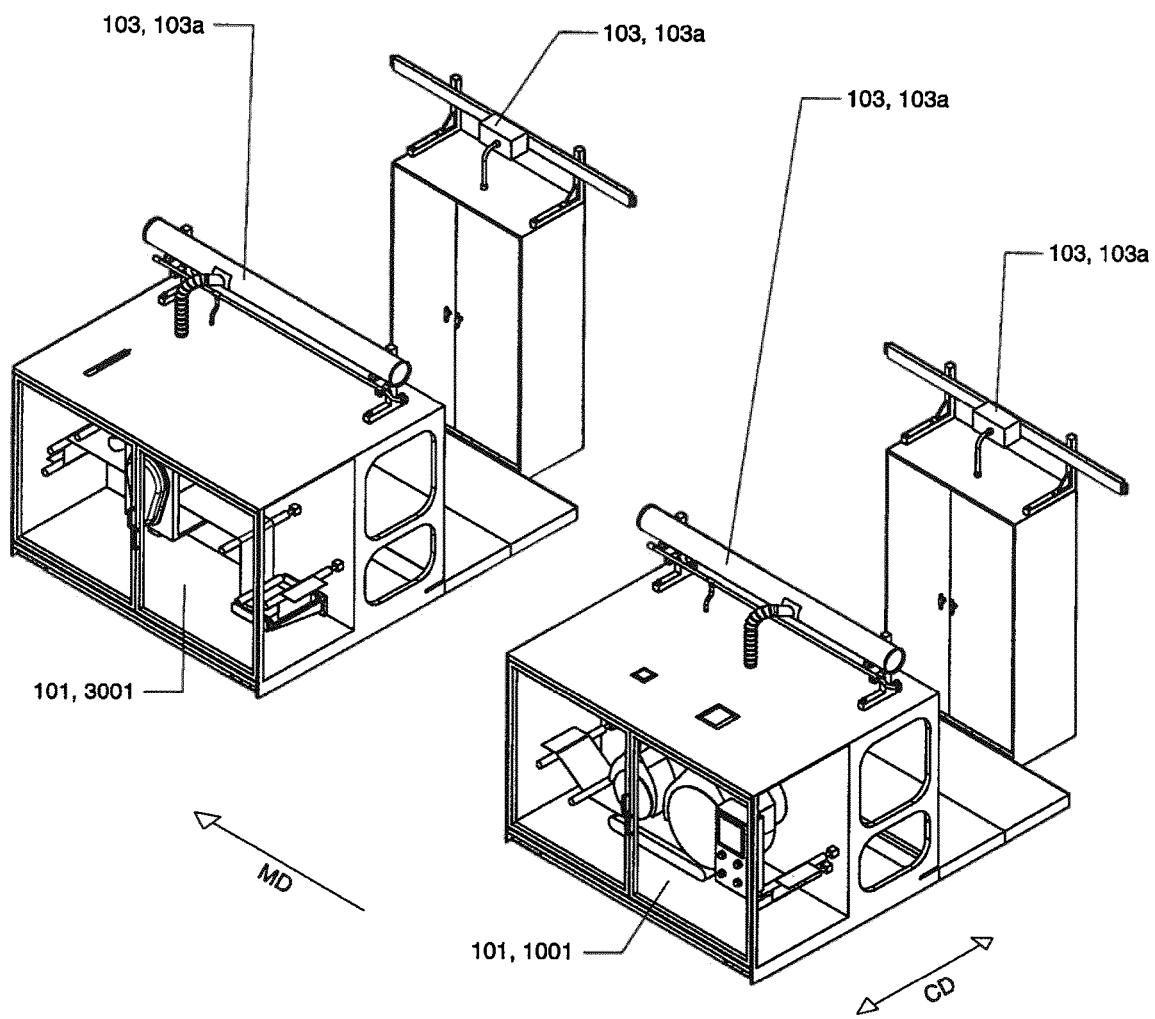
FIG. 16 is a detailed perspective view showing the middle converter module and associated accessory service modules removed from the arrangement shown FIG. 12.

As mentioned above, the releasable connections between adjacent converting modules 101 and accessory service modules 103 provide flexibility to the converting line 100 when removing, installing, and/or replacing converting modules 101 and/or accessory service modules 103. An example of such flexibility is discussed in more detail below with regard to FIGS. 13-16. In particular, FIG. 13 shows a detailed view of three converting modules 101 and associated accessory service modules 103 from the converting line 100 shown in FIG. 1. Specifically, FIG. 13 shows the second converting module 2001 and associated accessory service modules 103a, 103b connected with and between the first converting module 1001 and third converting module 3001 and respective accessory service modules 103, 103a. And FIGS. 14-16 show various configurations of the arrangement of FIG. 13 wherein the second converting module 2001 and/or associated accessory service modules 103 are removed. With regard to FIGS. 13-16, the middle accessory service modules refers to the accessory service modules 103a, 103b connect with the second converting module 2001.

On some occasions, such as during maintenance and/or installation activities or disassembly, it may be necessary or desirable to remove and/or replace a converting module 101 from the converting line 100. The releasable connections between adjacent converting modules 101 and accessory service modules 103 allows for the removal of a converting module 101 without having to remove associated accessory service modules 103. For example, as shown in FIG. 14, the second (middle) converting module 2001 is removed while the middle accessory service modules 103a, 103b remain connected with and supported between the accessory service modules 103a, 103b associated with and supported by the first converting module 1001 and the third converting module 3001. To remove the second converting module 2001 from FIG. 13 to arrive at the configuration shown in FIG. 14, the converting modules couplers 138, such as shown in FIGS. 7-9, may be disconnected and removed from between the second converting module 2001 and the first and third converting modules 1001, 3001. In addition, the support brackets 160 and duct couplers 166, such as shown in FIGS. 11 and 12 may be disconnected from the second converting module 2001. The second converting module 2001 may then be moved in CD direction out from between the first converting module 1001 and the third converting module 3001, leaving the middle accessory service modules 103a, 103b supported by the accessory service modules 103a, 103b associated with the first and third converting modules 1001, 3001. When desired, a second converting module 2001 can be reinserted into the converting line 100, and reconnected with adjacent converting modules 1001, 3001 and accessory service modules 103a, 103b.

In some situations, it may be necessary or desirable to remove and/or replace an accessory service module 103 from the converting line 100. The releasable connections between adjacent converting modules 101 and accessory service modules 103 allow for the removal of an accessory service module 103 without having to remove associated converting modules 101. For example, as shown in FIG. 15, the middle accessory service modules 103a, 103b are removed while the second converting module 2001 remains connected between the first and third converting modules 1001, 3001. To remove the middle accessory service module 103a, 103b from FIG. 12 to arrive at the configuration shown in FIG. 15, the accessory service module couplers 180, such as shown in FIGS. 11 and 12, may be disconnected and removed from between the middle accessory service modules 103a, 103b supported by the second converting module 2001 and the accessory service modules 103a, 103b supported by the first and third converting modules 1001, 3001. In addition, the support brackets 160 and duct couplers 166, such as shown in FIGS. 11 and 12 may be disconnected from the second converting module 2001.

The middle accessory service module may then be moved out from between the accessory service modules 103a, 1030b supported by the first and third converting modules 1001, 3001, leaving the second converting module 2001 in place between the first and third accessory service modules 1001, 3001. When desired, the middle accessory service modules 103a, 103b can be reinserted into the converting line 100, and reconnected with adjacent converting modules and accessory service modules.

In yet other instances, it may be necessary to remove and/or replace an accessory service module 103 and associated converting module 101 from the converting line. For example, as shown in FIG. 16, the middle accessory converting modules 103a, 103b and second converting module 2001 are removed, while the first and third converting modules 1001, 3001 and associated accessory service modules 103a, 103b remain installed on the converting line. To remove the middle accessory service modules 103a, 103b and second converting module 2001 from FIG. 12 to arrive at the configuration shown in FIG. 16, the converting modules couplers 138, such as shown in FIGS. 7-9, may be disconnected and removed from between the second converting module 2001 and the first and third converting modules 1001, 3001. In addition, the accessory service module couplers 180, such as shown in FIGS. 11 and 12, may be disconnected and removed from between the middle accessory service modules 103a, 103b and the adjacent accessory service modules 103a, 103b. The middle accessory service modules 103a, 103b and second converting module 2001 may then be moved in CD direction out from between the first and third converting modules 1001, 3001 and associated accessory service modules 103a, 103b. Once removed from the converting line 100, the middle accessory service modules 103a, 103b can be disconnected from the second converting module 2001. In other variations to the disassembly process above, the middle accessory converting modules may be removed from the converting line before removing the second converting module. In yet another variation, the second converting module may be removed from the converting line before removing second accessory service modules. When desired, middle accessory service modules 103a, 103b and converting module 2001 can be reinserted into the converting line and reconnected with adjacent converting modules and accessory service modules.

It is to be appreciated that the apparatuses and methods disclosed herein may be utilized with various different types and aspects of methods and apparatuses relating to converting lines, such as, for example, described in the U.S. patent application Ser. No. 12/544,363, entitled "RECONFIGURABLE CONVERTING LINE FOR FABRICATING ABSORBENT ARTICLES," filed on Aug. 20, 2009; U.S. patent application Ser. No. 12/544,268, entitled "SYSTEMS AND METHODS FOR CONTINUOUS DELIVERY OF WEB MATERIALS," filed on Aug. 20, 2009; U.S. patent application Ser. No. 12/544,291, entitled "FLEXIBLE MANUFACTURING SYSTEMS AND METHODS," filed on Aug. 20, 2009; and U.S. patent application Ser. No. 12/544,346, entitled "SPEED CHANGE KIT FOR AN ABSORBENT ARTICLE CONVERTING LINE," filed on Aug. 20, 2009, all of which are incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for fabricating disposable absorbent articles, the apparatus comprising:

a first converting module, a second converting module, and a third converting module, each converting module including a first wall and a second wall separated by a base and a top and defining an interior space, and wherein the each converting module defines a MD (machine direction) length, a CD (cross direction) width, and a height, and wherein each converting module is adapted to be arranged inside a shipping container, wherein the MD length of the converting module extending along an interior width of the shipping container, wherein the interior width of the shipping container is about 2350 mm;

a plurality of converting module couplers, the converting module couplers releasably connecting first converting module with the second converting module and releasably connecting the second converting module with the third converting module;

a first accessory service module, a second accessory service module, and a third accessory service module, each accessory service module comprising at least one utility duct selected from the group consisting of: a compressed air header duct, a vacuum air header duct, and an electrical power distribution bus duct, and wherein each accessory service module defines a MD length equal to or less than the MD length of each of the converting modules;

a plurality of accessory service module couplers comprising at least one quick-disconnect coupler selected from the group consisting of: bus-splice joint plate, flange pull ring locking collars, push-lock couplers, sliding sleeve couplers, cam and groove locking couplers, and flexible pipe hose clamps, the accessory service module couplers releasably connecting the first accessory service module with second accessory service module and connecting the second accessory service module with the third accessory service module;

wherein the first accessory module is supported by the first converting module such that the combination of the first accessory module and the first converting module defines a MD length equal to the MD length of the first converting module, wherein the second accessory module is supported by the second converting module such that the combination of the second accessory module and the second converting module defines a MD length equal to the MD length of the second converting module, and the third accessory module is supported by the third converting module such that the combination of the third accessory module and the third converting module defines a MD length equal to the MD length of the third converting module;

wherein the second converting module can be removed without removing the first and third converting modules and without removing the first, second, and third accessory modules such that the second accessory module is supported by the accessory module couplers when the second converting module is removed; and wherein the second accessory module can be removed without removing the first and third accessory modules and without removing the first, second, and third converting modules.

2. The apparatus of claim 1, wherein the first accessory service module is supported on the top of the first converting module, the second accessory service module is supported on the top of the second converting module, and the third accessory service module is supported on the top of the third converting module.

3. The apparatus of claim 1, further comprising:
a first absorbent article converting mechanism disposed in the interior space of the first converting module;
a second absorbent article converting mechanism disposed in the interior space of the second module; and
a third absorbent article converting mechanism disposed in the interior space of the third module.

4. The apparatus of claim 3, further comprising a plurality of duct couplers, the duct couplers releasably connecting the first absorbent article converting mechanism with the at least one utility duct of the first accessory service module, releasably connecting the second absorbent article converting mechanism with the at least one utility duct of the second accessory service module, and releasably connecting the third absorbent article converting mechanism with the at least one utility duct of the third accessory service module.

5. The apparatus of claim 1, wherein the MD length of each converting module is less than or equal to 2200 mm, the CD width of each converting module is less than or equal to 2890 mm, and the height of each converting module is less than or equal to 2275 mm.

6. The apparatus of claim 1, wherein the first converting module comprises:
a converting cabinet;
a controller cabinet; and
a cable tray connecting the converting cabinet with the controller cabinet.

7. The apparatus of claim 6, wherein the cable tray comprises a walkway.

8. The apparatus of claim 6, wherein the cable tray is reconfigurable between a first position and a second position, wherein the first converting module defines a first CD width when the cable tray is in the first position and wherein the first converting module defines a second CD width when the cable tray is in second position, and wherein the first CD width is less than the second CD width.

9. The apparatus of claim 8, wherein the cable tray is foldable, and wherein the first position is a folded position, and the second position is an extended position.

10. The apparatus of claim 8, wherein the cable tray is telescopically connected with the converting cabinet.

11. The apparatus of claim 6, further comprising a fourth accessory service module, and wherein the first accessory service module is releasably connected with the first converting cabinet and the fourth accessory service module is releasably connected with the controller cabinet.

12. The apparatus of claim 1, wherein the MD lengths of the converting modules are equal to each other.

13. A system for fabrication of disposable absorbent articles comprising:
a first converting module, a second converting module, and a third converting module, and wherein each converting module defines a MD (machine direction) length, a CD (cross direction) width, and a height, and wherein the MD lengths of modules are equal to each other,
a plurality of converting module couplers, the converting module couplers releasably connecting first converting module with the second converting module and releasably connecting the second converting module with the third converting module;
a first accessory service module, a second accessory module, and a third accessory module, each accessory module comprising at least one utility duct selected from the group consisting of: a compressed air header duct, a vacuum air header duct, and an electrical power distribution bus duct, and wherein each accessory service module defines a MD length equal to or less than the MD length of each of the converting modules;
a plurality of accessory service module couplers comprising at least one quick-disconnect coupler selected from the group consisting of: bus-splice joint plate, flange pull ring locking collars, push-lock couplers, sliding sleeve couplers, cam and groove locking couplers, and flexible pipe hose clamps, the accessory service module couplers releasably connecting the first accessory service module with second accessory service module and connecting the second accessory service module with the third accessory service module;
wherein the first accessory module is supported by the first converting module such that the combination of the first accessory module and the first converting module defines a MD length equal to the MD length of the first converting module, wherein the second accessory module is supported by the second converting module such that the combination of the second accessory module and the second converting module defines a MD length equal to the MD length of the second converting module, and the third accessory module is supported by the third converting module such that the combination of the third accessory module and the third converting module defines a MD length equal to the MD length of the third converting module;
wherein the second converting module can be removed without removing the first and third converting modules and without removing the first, second, and third accessory modules such that the second accessory module is supported by the accessory module couplers when the second converting module is removed; and
wherein the second accessory module can be removed without removing the first and third accessory modules and without removing the first, second, and third converting modules.

14. The apparatus of claim 13, wherein the first, second, and third converting modules are adapted to be arranged inside a single shipping container having an interior width of about 2350 mm, an interior length of about 12030 mm, and interior height of about 2700 mm, and wherein converting modules are arranged with the MD lengths of the converting modules extending along the interior width of the shipping container.

15. The apparatus of claim 13, wherein the first converting module comprises:
a converting cabinet;

a controller cabinet; and a cable tray connecting the converting cabinet with the controller cabinet.

16. The apparatus of claim 15, wherein the cable tray is reconfigurable between a first position and a second position, wherein the first converting module defines a first CD width when the cable tray is in the first position and wherein the first converting module defines a second CD width when the cable tray is in second position, and wherein the first CD width is less than the second CD width.

17. A method for shipping a converting line for fabricating disposable absorbent articles, the method comprising the steps of:

providing a first converting module, a second converting module, and a third converting module, and wherein each converting module defines a MD (machine direction) length, a CD (cross direction) width, and a height, the second converting module releasably connected with and between the first converting module and the third converting module;

providing a first accessory service module supported by the first converting module, a second accessory module supported by the second converting module, and a third accessory module supported by the third converting module;

disconnecting the second converting module from the first converting module and the third converting module;

removing the second converting module from between the first converting module and the third converting module; and supporting the second accessory service module from the first accessory service module and the third accessory service module.

18. The method of claim 17, further comprising the step of:

arranging the second converting module inside a shipping container having an interior width, an interior length greater than the interior width, and interior height, and wherein the second converting module is arranged with the MD length extending along the interior width of the shipping container.

19. The method of claim 18, wherein the second converting module comprises a converting cabinet, a controller cabinet, and a cable tray connecting the converting cabinet with the controller cabinet, wherein the cable tray is reconfigurable between a first position and a second position, and further comprising the step of:

reducing the CD width of the converting module by reconfiguring the cable tray from the first position to the second position.

20. The method of claim 19, wherein the step reducing the CD width further comprises folding the cable tray.

* * * * *